United States Patent
Ten Kate et al.

(10) Patent No.: US 11,292,768 B2
(45) Date of Patent: Apr. 5, 2022

(54) PROCESS FOR MANUFACTURING CHAIN-EXTENDED HYDROXYETHYLETHYLENEAMINES, ETHYLENEAMINES, OR MIXTURES THEREOF

(71) Applicant: NOURYON CHEMICALS INTERNATIONAL B.V., Arnhem (NL)

(72) Inventors: Antoon Jacob Berend Ten Kate, Arnhem (NL); Michiel Jozef Thomas Raaijmakers, Deventer (NL); Rens Veneman, Deventer (NL); Karl Fredrik Lake, Soedertaelje (SE); Robert Kristoffer Berg, Roenninge (SE); Eike Nicolas Kantzer, Uddevalla (SE); Rolf Krister Edvinsson, Partille (SE); Hendrik Van Dam, Arnhem (NL); Ina Ehlers, Stenungsund (SE)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/493,664

(22) PCT Filed: Mar. 12, 2018

(86) PCT No.: PCT/EP2018/056004
§ 371 (c)(1),
(2) Date: Sep. 12, 2019

(87) PCT Pub. No.: WO2018/166938
PCT Pub. Date: Sep. 20, 2018

(65) Prior Publication Data
US 2020/0131136 A1 Apr. 30, 2020

(30) Foreign Application Priority Data
Mar. 15, 2017 (EP) ..................................... 17161152

(51) Int. Cl.
C07D 233/34 (2006.01)
C07C 209/14 (2006.01)
C07C 213/08 (2006.01)

(52) U.S. Cl.
CPC .......... *C07D 233/34* (2013.01); *C07C 209/14* (2013.01); *C07C 213/08* (2013.01)

(58) Field of Classification Search
None
See application file for complete search history.

(56) References Cited

U.S. PATENT DOCUMENTS

| | | |
|---|---|---|
| 3,383,417 A | 5/1968 | Lichtenwalter |
| 4,503,250 A | 3/1985 | Herdle |
| 7,700,806 B2 | 4/2010 | van Cauwenberge et al. |

OTHER PUBLICATIONS

EPO, International Search Report and Written Opinion issued in International Application No. PCT/EP2018/056004, dated May 7, 2018.
EPO, International Preliminary Report on Patentability issued in International Application No. PCT/EP2018/056004, dated Jul. 11, 2019.

*Primary Examiner* — Joseph R Kosack
(74) *Attorney, Agent, or Firm* — Lorenz & Kopf, LLP

(57) ABSTRACT

The present disclosure pertains to a process for preparing hydroxyethylethyleneamines, ethyleneamines, or mixtures thereof, and/or ethylene urea derivatives thereof. The process includes reacting diethanolamine with an amine-functional compound that includes at least two —NH— units of which at least one is selected from the group of primary amine groups and cyclic secondary amine groups. The amine-functional compound includes at least one —NH—CH2-CH2-NH— unit wherein one or more —NH—CH2-CH2-NH— units in the amine-functional compound may be present in the form of cyclic ethylene urea moieties, piperazine moieties, or linear ethylene urea moieties, in the presence of a carbon oxide delivering agent.

19 Claims, No Drawings

PROCESS FOR MANUFACTURING CHAIN-EXTENDED HYDROXYETHYLETHYLENEAMINES, ETHYLENEAMINES, OR MIXTURES THEREOF

CROSS-REFERENCE TO RELATED APPLICATION

This application is a U.S. National-Stage entry under 35 U.S.C. § 371 based on International Application No. PCT/EP2018/056004, filed Mar. 12, 2018, which was published under PCT Article 21(2) and which claims priority to European Application No. 17161152.8, filed Mar. 15, 2019, which are all hereby incorporated in their entirety by reference.

TECHNICAL FIELD

The present disclosure pertains to a method for manufacturing chain-extended hydroxyethylethyleneamines, chain extended ethyleneamines, or mixtures thereof from a specific starting material.

BACKGROUND

Ethyleneamines includes of two or more nitrogen atoms linked by ethylene units. Ethyleneamines can be present in the form of linear chains H2N(—CH2-CH2-NH)p-H. For p=1, 2, 3, 4, . . . this gives, respectively, ethylenediamine (EDA), diethylenetriamine (DETA), linear triethylenetetramine (L-TETA), and linear tetraethylenepentamine (L-TEPA). It is clear that this range can be extended. With three or more ethylene units it is also possible to create branched ethyleneamines such as N(CH2-CH2-NH2)3, trisaminoethylamine (TAEA). Two adjacent nitrogen atoms can be connected by two ethylene units to form a piperazine ring —N(-)2-N—. Piperazine rings can be present in longer chains to produce the corresponding cyclic ethyleneamines.

Ethyleneamines, in particular diethylenetriamine (DETA) and higher ethyleneamines such as triethylenetetramine (TETA) are attractive products from a commercial point of view. In particular, the interest in higher ethyleneamines is increasing as these compounds have numerous commercial applications, e.g., as starting materials for, or use in, asphalt additives, corrosion inhibitors, epoxy curing agents, fabric softeners, fuel additives, hydrocarbon purification, ion exchange resins, lube oil additives, paper wet-strength resins, petroleum production chemicals, solvents, synthetic resins such as polyamide resins, mineral processing aids and interface-active substances (surfactants).

Hydroxyethylethyleneamines find application in chemical processes, as solvent or as reactant. For example, aminoethylethanolamine or AEEA of the formula H2N-CH2-CH2—NH—CH2-CH2-OH is an organic base used in the industrial manufacture of fuel and oil additives, chelating agents, and surfactants. Chain-extended ethanolamines, e.g., monoethanolamine compounds of the formula H2N—(CH2-CH2-NH)q-CH2-CH2-OH, wherein q is 2 or higher, are interesting intermediates for various types of organic synthesis, e.g., the manufacturing of esters of carboxylic acids. They can also be used in, for example, the formation of synthetic resins, as surfactants, for the production of emulsifiers, in fabric softeners, and as epoxy curing agents.

The manufacture of ethyleneamines is presently dominated by two routes, namely the reductive amination of monoethanolamine (MEA) and the ethylene dichloride (EDC) route.

The reductive amination of MEA takes place in the presence of a hydrogenation/dehydrogenation catalyst in an excess of ammonia. Next to the reductive amination of MEA to give EDA a number of side reactions, including transamination, produce a mixture of a large number of ethylene and ethanolamines. The output is dominated by mono and diethylene products (EDA, DETA, piperazine (PIP), and AEEA). Higher ethylene and ethanolamines are also formed but the mixture is complex and ineffective in producing high yields of the most important higher ethyleneamines TETA and TEPA.

Several attempts to use transamination to produce ethyleneamines with two or more ethylene units have been reported but seem limited to the diethylene compound DETA.

The EDC route is the substitution reaction of EDC (ethylene dichloride) with ammonia and/or another ethyleneamine at elevated temperatures and pressures to form hydrochlorides which are then reacted with caustic to generate mixtures of ethyleneamines and NaCl. Today, the EDC-based process is the main process for producing higher polyethylenepolyamines. The EDC route is fully dependent on the use of ethylene dichloride which is expensive, difficult to handle, and surrounded by HSE issues. Additionally, the EDC route gives a mixture of many different polyethylenepolyamines. Furthermore the EDC route results in the formation of substantial amounts of NaCl which may result in corrosion and the formation of colored products.

Various processes for manufacturing hydroxyethylethyleneamines have been described.

For example, U.S. Pat. No. 3,383,417 describes the manufacture of aminoethylethanolamine by reaction of monoethanolamine with itself in the presence of a catalyst comprising nickel, copper, and a minor amount of chromium oxide, manganese oxide, molybdenum oxide, and thorium oxide.

U.S. Pat. No. 7,700,806 describes a process for preparing ethyleneamines and ethanolamines by hydrogenative amination of monoethyleneglycol and ammonia in the presence of a catalyst. The process is carried out in two stages, wherein in the first stage the amination is carried out over a hydroamination catalyst to a monoethyleneglycol conversion of not more than 40%, and in the second stage the reaction is carried out over a supported catalyst comprising ruthenium and cobalt with a specific particle shape.

There is need in the art for a process for manufacturing chain-extended hydroxyethylethyleneamines. There is also need in the art for a process for manufacturing higher ethyleneamine compounds, in particular tetraethylenepentamine and other higher ethyleneamines, which process shows a high yield and limited formation of lower ethyleneamines. It would be particularly attractive if such a process could use starting materials which are commercially available at a reasonable price.

BRIEF SUMMARY

Processes for preparing hydroxyethylethyleneamines, ethyleneamines, or mixtures thereof, and/or ethylene urea derivatives thereof are provided. In an exemplary embodiment, the process includes reacting diethanolamine with an amine-functional compound that includes at least two —NH— units of which at least one is selected from the group of primary amine groups and cyclic secondary amine groups. The amine-functional compound includes at least one —NH—CH2-CH2-NH— unit wherein one or more —NH—CH2-CH2-NH— units in the amine-functional compound is present in the form of cyclic ethylene urea moieties, piperazine moieties, or linear ethylene urea moieties, in the presence of a carbon oxide delivering agent. The molar ratio of amine-functional compound to diethanolamine is at least about 0.2:1. The molar ratio of carbon oxide delivering agent to —NH—CH2-CH2-NH— units in the amine-functional compound is at least about 0.1:1.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure provides such a process.

The present disclosure pertains to a process for preparing hydroxyethylethyleneamines, ethyleneamines, or mixtures thereof, and/or ethylene urea derivatives thereof comprising the step of reacting diethanolamine with an amine-functional compound comprising at least two —NH— units of which at least one is selected from the group of primary amine groups and cyclic secondary amine groups, the amine-functional compound comprising at least one —NH—CH2-CH2-NH— unit wherein one or more —NH—CH2-CH2-NH-units in the amine-functional compound may be present in the form of cyclic ethylene urea moieties, piperazine moieties, or linear ethylene urea moieties, in the presence of a carbon oxide delivering agent, wherein
 the molar ratio of amine-functional compound to diethanolamine is at least 0.2:1, and
 the molar ratio of carbon oxide delivering agent to —NH—CH2-CH2-NH— units in the amine-functional compound is at least about 0.1:1.

It has been found that the process as contemplated herein makes it possible to obtain higher ethyleneamines and higher hydroxyethylethyleneamines, and urea derivatives of these compounds, via a process which makes use of an attractive starting material, with relatively high yield and relatively low formation of lower ethyleneamines, without having to use ammonia, releasing ammonia, or having to use metal-containing catalysts.

Diethanolamine is an attractive starting material because it is commercially available as a product from the reaction of ethylene oxide with ammonia. In that process, the monoethanolamine which is the primary reaction product of ethylene oxide with ammonia can react with additional ethylene oxide to form diethanolamine and triethanolamine. Because diethanolamine reacts much slower than monoethanolamine in the catalytic reductive amination process it is currently not used as starting material for making ethyleneamines. The present disclosure makes it possible to do so.

Further advantages of the process as contemplated herein and specific embodiments thereof will become apparent from the further specification.

It is noted that U.S. Pat. No. 4,503,250 describes a process for preparing predominantly linear polyalkylenepolyamines by reacting ammonia or an alkyleneamine compound having two primary amine groups with an alcohol or an alkanolamine in the presence of a derivative of carbonic acid at a temperature at which the reaction will proceed under pressures sufficient to maintain the reaction mixture in the liquid phase. This document contains two examples in which diethanolamine is used as starting material. In both cases, the diethanolamine is reacted with urea, to form diethylenetriamine. Reaction with an amine-functional compound comprising at least one —NH—CH2-CH2-NH— unit is not described, so higher amines are not formed.

The present disclosure will be discussed in more detail below.

Diethanolamine is used as starting material. This compound can be provided as such, or at least in part in the form of a CO adduct. Examples of CO adducts are linear CO adducts, e.g., compounds of the formula HO-CH2-CH2-NH—CH2-CH2-O—C(O)—O-CH2-CH2-NH—CH2-CH2-OH, and cyclic CO adducts, such as urea derivatives.

Carbon oxide delivering agents suitable for use in the present disclosure are compounds which are able to provide carbonyl groups under reaction conditions. Organic compounds in which a carbonyl group is available include urea and derivatives thereof; linear and cyclic alkylene ureas, especially cyclic urea, mono or di-substituted alkylene ureas, alkyl and dialkyl ureas, linear and cyclic carbamates, organic carbonates and derivatives or precursors thereof. Such derivatives or precursors may for example include ionic compounds such as carbonate or bicarbonate salts that can be converted, in some embodiments in situ, in the process as contempleted herein into their non-ionic counterparts, for example into linear and cyclic carbamate or urea compounds. Preferably, when such ionic compounds are used in the present disclosure, they are organic hydrocarbon-based carbonate or bicarbonate salts. Preferably the organic compounds that are suitable for use as carbon oxide delivering agents are those wherein alkylene is ethylene. The carbon oxide delivering agent can be present in the process in the same molecule as the amine-functional or the diethanolamine compound.

It is preferred for the carbon oxide delivering agent to be such that it does not provide additional organic compounds to the reaction mixture than diethanolamine and the amine-functional compound.

Accordingly, the carbon oxide delivering agent used in the present disclosure includes carbon dioxide, adducts of carbon dioxide with diethanolamine, such as the compounds discussed above, and adducts of carbon dioxide with amine-functional compounds.

Examples of suitable carbonyl adducts of amine-functional compounds include ethylene urea (EU), diaminoethylene urea (DAEU), which is the linear carbonyl adduct of two ethylene diamine molecules, the cyclic urea derivative of diethylenetriamine (UDETA), and cyclic urea derivatives of triethylenetetramine, such as the cyclic urea derivative of triethylenetetramine, with the carbonyl group added to the terminal H2N-CH2-CH2-NH moiety (U1TETA) and the cyclic diurea additive of triethylenetetramine (DUTETA).

Examples of carbon oxide delivering agents include:

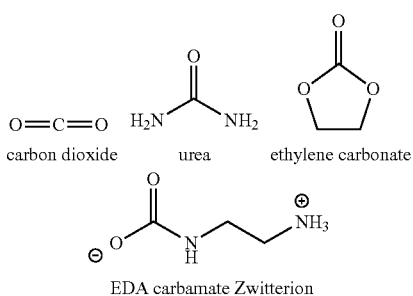

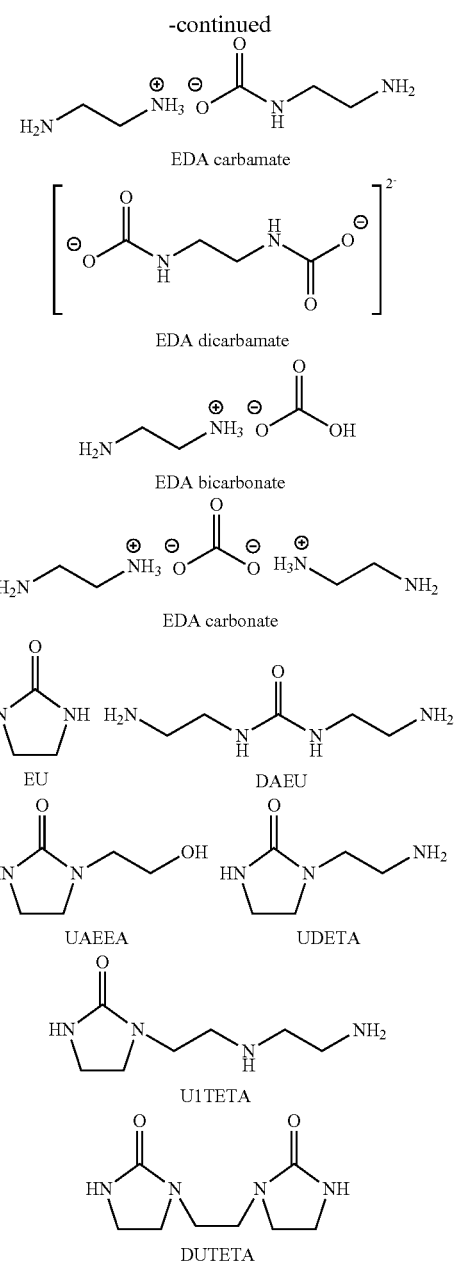

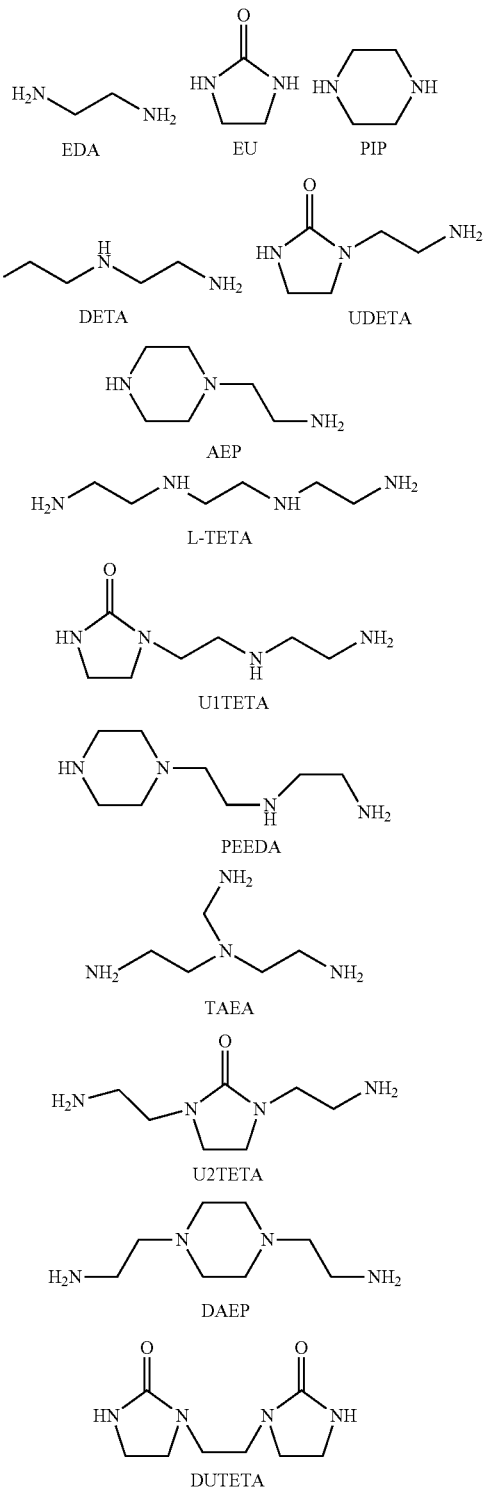

a urea derivative). The amine functional compound comprises at least one —NH—CH2-CH2-NH— unit, as such or in the form of a piperazine or urea derivative.

Some examples of suitable amine-functional compounds are shown below as illustration. As will be clear to the skilled person, this can be extended to include pentamines, hexamines and so on.

The use of a carbon oxide delivering agent selected from the group of carbon dioxide, CO adducts of diethanolamine, and ethylene urea (EU) and other urea adducts of amine compounds may be particularly preferred. Of course, combinations of the various types of carbon oxide delivering agents may be applied, if so desired.

The present disclosure makes use of an amine-functional compound as starting material. The amine-functional compound comprises at least two —NH— units of which at least one, in particular two (or more, if more are present), is selected from the group of primary amine groups and cyclic secondary amine groups. Cyclic secondary amine groups can be found in urea derivatives or piperazines. It is preferred in the amine-functional compound for the nitrogen atoms to be connected to each other via an ethylene chain (—CH2-CH2-), via a carbonyl group (—C(O)—), via two ethylene chains (therewith forming a piperazine ring), or via an ethylene chain and a carbonyl group (therewith forming

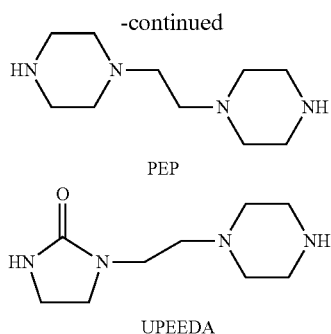

PEP

UPEEDA

EDA Ethylenediamine
EU Ethylene urea
PIP Piperazine
DETA Diethylenetriamine
UDETA Cyclic urea derivative of diethylenenetriamine
AEP Aminoethylpiperazine
L-TETA Linear triethylenetetramine
U1TETA Cyclic urea derivative of triethylenetetramine, with the carbonyl group added to the terminal H2N-CH2-CH2-NH moiety
PEEDA Piperazinoethylethylenediamine
TAEA Trisaminoethylamine
U2TETA Cyclic urea adduct of triethylenetetramine, with the carbonyl group added to the central NH—CH2-CH2-NH moiety
DAEP Diaminoethylpiperazine
DUTETA Cyclic diurea adduct of triethylenetetramine
PEP Piperazinoethylpiperazine
UPEEDA Cyclic urea adduct of piperazinoethylethylenediamine As indicated above, the amine-functional compound comprises at least one —NH—CH2-CH2-NH— unit, wherein the —NH—CH2-CH2-NH— units in the amine-functional compound may be present in the form of a cyclic ethylene urea moiety or a piperazine moiety. EDA, EU, DETA and UDETA may be mentioned as preferred compounds, with EDA and EU being particularly preferred. PIP and AEP may also be attractive. PIP has been found to be particularly attractive for the manufacture of cyclic ethyleneamine compounds.

In one embodiment, the amine-functional compound and the carbon oxide delivering agent are added at least partly as one compound in the form of a urea adduct.

In the process as contemplated herein, the molar ratio of amine-functional compound to diethanolamine is at least about 0.2:1. If the molar ratio of amine-functional compound to diethanolamine is below about 0.2:1, insufficient conversion will be obtained. In general, increasing the molar ratio of amine-functional compound to diethanolamine will lead to increased conversion. Therefore, it may be preferred for the molar ratio of amine-functional compound to diethanolamine to be at least about 0.5:1, in particular at least about 1:1. If it is desired to manufacture substantial amounts of ethyleneamines, higher ratios may be preferred. Therefore, in some embodiments of the present disclosure, the molar ratio of amine-functional compound to diethanolamine is at least about 1.5:1, in particular at least about 2:1, or at least about 2.5:1. Going to very high molar ratios of amine-functional compound to diethanolamine may not increase selectivity, while it will lead to a diluted system. Therefore, in general the molar ratio of amine-functional compound to diethanolamine is at most about 10:1.

In the process as contemplated herein the molar ratio of carbon oxide delivering agent to —NH—CH2-CH2-NH— units in the amine-functional compound is at least about 0.1:1. If the value is below this range, conversion will be too low. It is preferred for the molar ratio of carbon oxide delivering agent to —NH—CH2-CH2-NH— units to be at least about 0.5:1. It may be preferred for the ratio to be at least about 0.7:1, even more preferred at least about 1:1, as this means that all —NH—CH2-CH2-NH groups in the amine compound can be present in the form of urea groups. The maximum ratio is not critical. An upper limit of about 5:1 may be mentioned in general. A maximum ratio of about 3:1 may be attractive in commercial operation. There may be an optimum for the molar ratio of carbon oxide delivering agent to —NH—CH2-CH2-NH— units, depending on reaction temperature, reaction time, and ratios between the various components.

In this context a —NH—CH2-CH2-NH— unit is a unit which can form an ethylene urea unit in the amine-functional compound. For example, ethylenediamine (NH2-CH2-CH2-NH2) contains one —NH—CH2-CH2-NH— unit. Diethylenetriamine (NH2-CH2-CH2-NH—CH2-CH2-NH2) also contains one —NH—CH2-CH2-NH— unit, since the middle NH unit can be part of only one —NH—CH2-CH2-NH— unit. Triethylenetetramine (NH2-CH2-CH2-NH—CH2-CH2-CH2-NH—CH2-CH2-NH2) contains two —NH—CH2-CH2-NH— units.

In principle, the molar ratio of carbon oxide delivering agent to diethanolamine ratio follows from the molar ratio of amine-functional compound to diethanolamine and the molar ratio of carbon oxide delivering agent to —NH—CH2-CH2-NH— units in the amine-functional compound. In general, it may be preferred for the molar ratio of carbon oxide delivering agent to diethanolamine to be at least about 0.1:1, in particular at least about 0.5:1, more in particular between about 0.5:1 and about 10:1.

Higher ratios of carbon oxide delivering agent to diethanolamine in combination with higher amine to diethanolamine ratios may favour the production of ethyleneamine products.

In one embodiment, the CO delivering agent also provides part of or the entirety of the diethanolamine in the form of a CO-adduct of diethanolamine and/or the CO-delivering agent also provides part of or the entirety of the amine-functional compound. It may be preferred to add at least about 50% of the CO in the form of a CO adduct of diethanolamine or in the form of a CO adduct of the amine-functional compound, in particular at least about 75%, more in particular at least about 90%. In one embodiment, at least about 95%, or essentially all, of the CO is added in the form of either a CO adduct of diethanolamine and/or in the form of a CO adduct of the amine-functional compound.

In this case the maximum molar ratio of the CO delivering compound to the number of ethylene groups present in the system as diethanolamine and —NH—CH2-CH2-NH— units in the amine-functional compound is about 1:1.

The process as contemplated herein can be used to manufacture ethylenediamines, urea and piperazine derivatives thereof, and adducts thereof using CO2.

In one embodiment, the reaction product comprises alkanolamines of the formula H2N—(CH2-CH2-NH)q-CH2-CH2-OH, wherein q has a value of 2-10, in particular 2-5, more in particular 2-4, preferably 2 or 3, and wherein one or more —NH—CH2-CH2-NH— units may be present as a cyclic ethylene urea unit

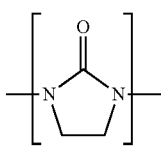

or piperazine unit,

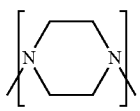

and wherein one or more —NH—CH2-CH2-OH units may be present as cyclic ethylene carbamate unit

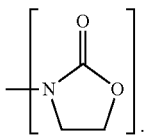

In one embodiment one or more alkanolamines or derivatives thereof as specified above are connected to each other via a linear ethylene urea structure, e.g. as follows:

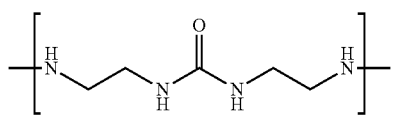

In one embodiment, the reaction product comprises ethyleneamines of the formula H2N—(CH2-CH2-NH-)p-H wherein p is at least 4, or derivatives thereof wherein one or more —NH—CH2-CH2-NH— units may be present as cyclic ethylene urea unit

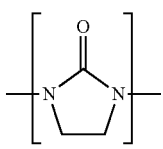

and/or piperazine unit

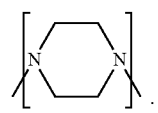

In one embodiment one or more ethyleneamines or derivatives thereof as specified above are connected to each other via a linear ethylene urea structure, e.g. as follows:

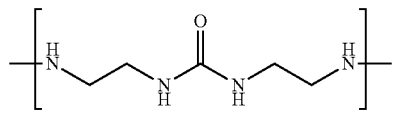

It may be preferred for p to be at most 10, in particular at most 8.

In one embodiment of the present disclosure, the amine-functional compound comprises ethylenediamine (EDA), ethylene urea (EU), or a mixture thereof, and the reaction product comprises hydroxyethyldiethylenetriamine (HE-DETA) of the formula H2N—(CH2-CH2-NH)q-CH2-CH2-OH wherein q is 2 and/or urea and carbamate derivatives thereof, and/or tetraethylenepentamine (TEPA) of the formula H2N—(CH2-CH2-NH-)p-H wherein p is 4, and/or urea derivatives thereof.

In one embodiment of the present disclosure, the amine-functional compound comprises diethylenetriamine (DETA), the urea adduct thereof (UDETA), or a mixture thereof, and the reaction product comprises hydroxyethyltriethylenetetramine (HE-TETA) of the formula H2N—(CH2-CH2-NH)q-CH2-CH2-OH wherein q is 3, and/or urea and carbamate derivatives thereof and/or hexaethyleneheptamine (HEHA) of the formula H2N—(CH2-CH2-NH-)p-H wherein p is 6, and/or urea derivatives thereof.

In one embodiment of the present disclosure, the amine-functional compound comprises piperazine (PIP) and the reaction product comprises hydroxyethyleneaminoethylpiperazine (HEAEPIP) and/or piperazinoethylaminoethylpiperazine (PEAEP).

It should be noted that the relative ratios between the various components are to be calculated based on the compounds diethanolamine, carbon dioxide, and amine-functional compound, irrespective of the form in which they are added. For example, one mole ethylene urea should be regarded as being equivalent to one mole carbon dioxide and one mole ethylenediamine. For another example, one mole of the diurea adduct of triethylenetetramine (DUTETA) should be regarded as being equivalent to two moles carbon dioxide delivering agent and one mole triethylenetetramine.

The reaction is carried out by combining the various components and bringing the mixture to reaction conditions.

Reaction conditions include a reaction temperature which is generally at least about 100° C. The temperature should preferably be lower than about 400° C. More preferably the temperature is between about 150 and about 360° C. Even more preferably the temperature is between 180 and 340° C. Most preferably the temperature is between about 200 and about 310° C. It has been found that higher temperatures favor the conversion to ethyleneamine compounds.

The reaction is carried out at a pressure which is such that the reaction mixture is in the liquid phase. It will therefore depend on the reaction temperature. In general, the reaction pressure will be between about 1 and about 60 bar.

The reaction time during the process is in an embodiment between about 5 minutes and about 40 hours, preferably between about 0.5 and about 25 hours, more preferably between about 1 and about 18 hours.

The process of the present disclosure can be done with or without any additional liquid present. If a liquid is added to the reaction system, the liquid preferably is a polar liquid, such as an alcohol or water. Doing the process of the present disclosure in the presence of water as a liquid or without any additional liquid is preferred.

The reactor employed can be any suitable reactor including continuously stirred tank reactor, pipeline reactor, tubular or multi-tubular reactor. The reactor may be adiabatic or equipped with external or internal heating devices. Feed may be single point or split into multiple points. It can include or otherwise consist of multiple stages with inter-stage heat exchange.

The process can be carried out in a batch reactor, possibly fed-batch operation, or in a continuously operating system in one reactor or in a cascade of continuous flow reactors. The reactor can be a single reaction unit or a set of reaction units. The reaction and separation can be performed in separate steps or at least partially simultaneously. The reaction and separation can involve multiple reaction steps with separation steps in between.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

The person skilled in the art is capable of selecting the proper reactor and separation unit scheme by determining the overall yield, energy consumption and waste production.

The product mixture can be further processed or fractionated into several products that each independently are either pure compounds or mixture of compounds, some of which may be recycled.

The reaction product will comprise one or more compounds in the form of urea adducts. In one embodiment, the product is subjected to a CO removal reaction to convert the urea adduct into amine compounds. Within the context of the present specification, a CO removal reaction is intended to refer to any reaction wherein the urea adduct is converted into the corresponding amine compound by removal of the carbonyl group and addition of two hydrogen atoms.

In the present specification, mention is made of urea adducts and urea derivatives. These terms are used interchangeably to refer to compounds wherein two nitrogen atoms are connected through a —C(O)— moiety. The terms CO adducts and CO2 adducts are also used interchangeably. They refer to compounds wherein either two nitrogen atoms are connected through a —C(O)— moiety or a nitrogen atom and an oxygen atom are connected through a —C(O)— moiety.

The present disclosure will be elucidated by the following examples, without being limited thereto or thereby.

Example 1: Reaction of DEA with EDA or the Urea Adduct Thereof

A number of experiments were carried out as follows:
In the following: DEA stands for diethanolamine, EDA stands for ethylenediamine, EU stands for ethylene urea, HEDETA stands for hydroxyethyldiethylenetriamine, (U)HEDETA stands for hydroxyethyldiethylenetriamines, as such or in the form of urea adducts and Σ(U)HEDETAs stands for the total amount of hydroxyethyldiethylenetriamines, as such or in the form of urea adducts. (U)TEPA stands for tetraethylenepentamines, as such or in the form of urea adducts and Σ(U)TEPAs stands for the total amount of tetraethylenepentamines, as such or in the form of urea adducts. GC-FID stands for gas chromatography using a flame ionization detector.

Example 1A: Production of (U)HEDETA

DEA (12.1 g, 115 mmol), EDA (1.8 g, 30 mmol), and EU (9.90 g, 115 mmol) were added to a pressure reactor. The reactor was put under an atmosphere of N2 and was heated to 270° C. during 1 h and kept at 270° C. for 4 h. The reactor was cooled to ambient temperature and the resulting mixture was analyzed by GC-FID.

Example 1B: Production of (U)HEDETA

DEA (9.0 g, 86 mmol), EDA (5.1 g, 86 mmol), and EU (7.4 g, 86 mmol) were added to a pressure reactor. The reactor was put under an atmosphere of N2 and was heated to 270° C. during 1 h and kept at 270° C. for 4 h. The reactor was cooled to ambient temperature and the resulting mixture was analyzed by GC-FID.

Example 1C: Production of (U)HEDETA at High Selectivity Versus (U)TEPA

DEA (12.0 g, 114 mmol), EDA (1.72 g, 29 mmol), and EU (9.8 g, 114 mmol) were added to a pressure reactor. The reactor was put under an atmosphere of N2 and was heated to 240° C. during 1 h and kept at 240° C. for 4 h. The reactor was cooled to ambient temperature and the resulting mixture was analyzed by GC-FID.

Example 1D: Production of (U)TEPA

DEA (9.0 g, 86 mmol), EDA (2.6 g, 43 mmol), and EU (18.4 g, 214 mmol) were added to a pressure reactor. The reactor was put under an atmosphere of N2 and was heated to 270° C. during 1 h and kept at 270° C. for 4 h. The reactor was cooled to ambient temperature and the resulting mixture was analyzed by GC-FID.

Example 1E: Production of (U)TEPA

DEA (7.0 g, 66 mmol), EDA (4.0 g, 67 mmol), and EU (17.2 g, 200 mmol) were added to a pressure reactor. The reactor was put under an atmosphere of N2 and was heated to 270° C. during 1 h and kept at 270° C. for 4 h. The reactor was cooled to ambient temperature and the resulting mixture was analyzed by GC-FID.

The results are summarized in Table 1.

TABLE 1

| | Example | | | | |
| --- | --- | --- | --- | --- | --- |
| | 1A | 1B | 1C | 1D | 1E |
| Amine:DEA molar ratio | 1.25:1 | 2:1 | 1.25:1 | 3:1 | 4:1 |
| CO:DEA molar ratio | 1 | 1 | 1 | 2.5 | 3 |
| CO:(HN—CH2—CH2—NH) ratio | 0.80 | 0.50 | 0.80 | 0.83 | 0.75 |
| Temp. (° C.) | 270 | 270 | 240 | 270 | 270 |
| EDA | 7.7 | 20.7 | 9.2 | 10.8 | 13.0 |
| EU | 8.8 | 9.3 | 22.1 | 24.5 | 29.9 |

TABLE 1-continued

| | Example | | | | |
|---|---|---|---|---|---|
| | 1A | 1B | 1C | 1D | 1E |
| DEA | 4.9 | 9.9 | 26.3 | n.d. | n.d. |
| Σ(U)HEDETAs | 15.6 | 15.5 | 14.7 | 10.2 | 10.5 |
| Σ(U)TEPAs | 5.2 | 4.9 | 1.3 | 14.4 | 14.3 |
| Conv to (U)HEDETAs (in %) | 19.6 | 27.2 | 18.8 | 20.6 | 25.6 |
| Conv to (U)TEPAs (in %) | 4.5 | 5.5 | 1.1 | 21.6 | 26.1 |

All GC-FID data in wt-%
n.d. = not detected (i.e. below detection limits)

Conv stands for the conversion of diethanolamine into the cited compounds, calculated as mole product per mole starting diethanolamine.

Example 1A afforded 15.6 wt % of (U)HEDETA and 5.2 wt % of (U)TEPA. Increasing the amine excess to 2:1 (example 1B) afforded similar wt % of the two products but a higher conversion rate to (U)HEDETA (note that the reaction mixture contained more amine, so that the same weight percentage of product corresponds to a higher yield calculated on starting material).

Lowering the reaction temperature to 240° C. at an amine:DEA ratio of 1.25 offered an improved selectivity of (U)HEDETA relative to (U)TEPA (example 1C).

Increasing the amine and CO excess relative to DEA (example 1D) resulted in predominantly (U)TEPA product at 14.4 wt %.

Increasing the excess of both amine and CO relative to DEA afforded a higher conversion to (U)TEPA.

A CO:DEA ratio of 1:1 and an amine:DEA ratio of 1.25-2.0:1 will favor (U)HEDETA over (U)TEPA. Selectivity can be improved by lowering the reaction temperature. Increasing the amine:DEA ratio to 3-4:1 and the CO:DEA ratio 2.5-3:1 shifts the product distribution in favor of (U)TEPA.

Example 2: Reaction of DEA with PIP and CO2

Experiments were carried out as follows: The reagents were charged to 7 mL pressure vessels, the vessels were sealed and CO2 was added with a syringe pump. The reaction vessels were placed in a modified GC oven and heated to 180 to 250° C. for 2 to 16 h. At the end of the reactions, the vessels were cooled to 70° C. and carefully depressurized. The end-cap was opened and $H_2O$ was added to dissolve the reaction mixture. The solutions were analyzed by GC-FID and are reported as GC peak area-%. Identity of GC peaks was determined by GC-MS using chemical and/or electron ionization. The reaction was carried out at 220° C. using a molar ratio of DEA/PIP/$CO_2$ of 1:2:2.

The main products are thought to form via the following reaction scheme:

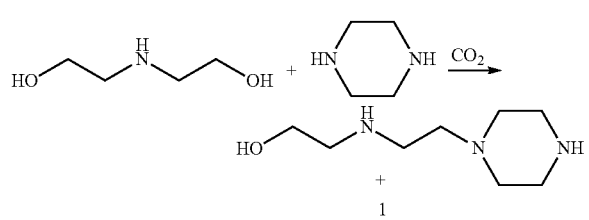

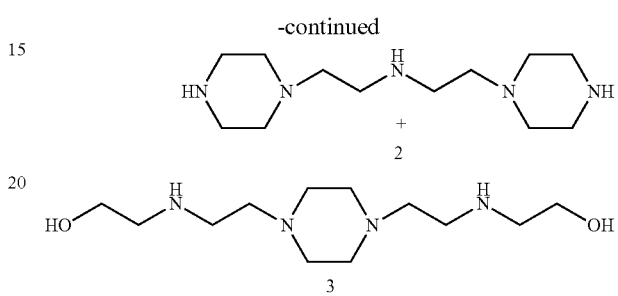

As can be seen from the table below, after 4 h the main product with 28% yield was 1 (HEAEPIP, hydroxyethyleneaminoethylpiperazine—where one PIP unit has been introduced into DEA—but dicyclic TEPA 2 (PEAEP, piperazinoethylaminoethylpiperazine) is also observed with 7% yield, as well as PIP that reacted with two DEA molecules 3 (Bis-HEAEPIP, bis-hydroxyethyleneaminoethylpiperazine) (1.9% yield). Extending the reaction time to 16 h results in higher conversion and especially higher yield of dicyclic TEPA (22.7%).

TABLE 2

| | Example | |
|---|---|---|
| | 2A | 2B |
| Amine:DEA molar ratio | 2:1 | 2:1 |
| CO:DEA molar ratio | 1 | 1 |
| CO:(HN—CH2—CH2—NH) ratio | 1 | 1 |
| Temp. (° C.) | 220 | 220 |
| Reaction time (h) | 4 | 16 |
| PIP | 44.2 | 28.4 |
| DEA | 10.8 | 0.4 |
| HEAEPIP (1) | 28.2 | 13.6 |
| PEAEP (2) | 7.0 | 22.7 |
| Bis-HEAEPIP (3) | 1.9 | n.d. |

All GC-FID data in area-%
n.d. = not detected (i.e. below detection limits)

Example 3: Reaction of DEA with UDETA and CO2

DEA (3.1 g, 29 mmol) and UDETA (10.6 g, 75 mmol) were added to a pressure reactor. The reactor was put under an atmosphere of N2 and CO2 (gaseous, 3.7 g, 84 mmol) was added. The mixture was heated to 220° C. during 50 min and kept at 220° C. for 6 h. The reactor was cooled to ambient temperature and the resulting mixture was analyzed by GC-FID and liquid chromatography coupled with mass spectroscopy (LC-MS).

The following overview shows the two main products which are formed via the reaction of DEA with UDETA and CO2:

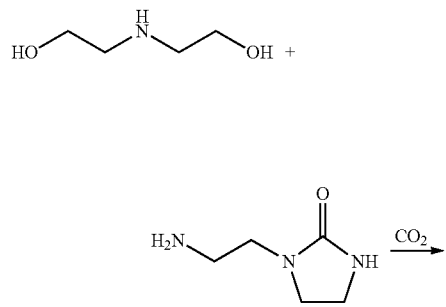

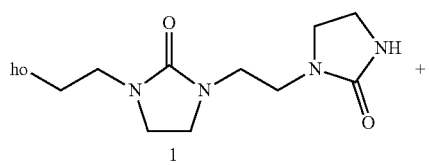

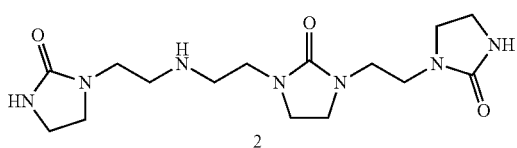

TABLE 3

|  | Example 3 |
|---|---|
| Amine:DEA molar ratio | 2.5:1 |
| CO:DEA molar ratio | 5.4:1 |
| CO:(HN—CH2—CH2—NH) ratio | 1.06:1 |
| Temp. (° C.) | 220 |
| Reaction time (h) | 6 |
| UDETA | 27.8 |
| DEA | n.d. |
| HEDUTETA (1) (main isomer) | 22.1 |
| TUHEHA (2) | 12.9 |

All GC-FID data in area-%
n.d. = not detected (i.e. below detection limits)

Besides the compounds listed in Table 3, 6 area-% of DUTETA and 19 area-% of pentaethylhexamine (PEHA) containing three cyclic urea groups were found.

Example 4: Reaction of DETA with EU and EDA

Experiments were carried out under the same conditions as described above for Example 1A, but using the amounts of material specified in Table 4 below. Table 4 also provides the results of the product analysis.

TABLE 4

| | Experiment | | | | | |
|---|---|---|---|---|---|---|
| | 4A[6] | 4B[6] | 4C[6] | 4D[6] | 4E[6] | 4F |
| Reaction Mixture | | | | | | |
| DEA (mol)[1] | 1 | 1 | 1 | 1 | 1 | 1 |
| EDA (mol)[1] | 0 | 0.1 | 0.14 | 1.2 | 1.15 | 0.625 |
| EU (mol)[1] | 0.15 | 0.05 | 0.01 | 0.05 | 0.10 | 0.625 |
| Amine:DEA[2] | 0.15:1 | 0.15:1 | 0.15:1 | 1.25:1 | 1.25:1 | 1.25:1 |
| CO:(HN—CH$_2$—CH$_2$—NH)[3] | 1:1 | 0.33:1 | 0.07:1 | 0.04:1 | 0.08:1 | 0.5:1 |
| Product Analysis[4] | | | | | | |
| EDA | 0.66% | 2.37% | 1.91% | 30.91% | 24.82% | 13.71% |
| PIP | — | — | 0.57% | 0.64% | 0.49% | — |
| DEA | 40.36% | 75.79% | 78.60% | 60.21% | 58.28% | 25.41% |
| EU | — | — | — | 0.55% | 0.99% | 4.49% |
| AEP | 0.53% | 0.58% | 0.91% | — | 0.47% | 0.40% |
| diHEP[5] | 13.83% | 4.20% | 2.37% | 0.33% | 0.94% | 6.27% |
| Σ(U)HEDETAs | 2.35% | 0.75% | 0.51% | 4.04% | 5.57% | 16.83% |
| Σ(U)TEPAs | 2.62% | 0.43% | — | — | — | 1.87% |
| Conversion to (U)HEDETAs | 1.66% | 0.58% | 0.39% | 4.39% | 6.02% | 18.07% |
| Conversion to (U)TEPAs | 1.41% | 0.23% | — | — | — | 1.43% |

[1]number of moles relative to moles DEA used
[2]molar ratio of amine functional compound (EDA + EU) to DEA
[3]molar ratio of carbon oxide delivering agent (EU) to NH—CH$_2$—CH$_2$—NH groups in the amine functional compound (EU + EDA)
[4]percentages are wt %
[5]diHEP = 2 di-(hydroxyethyl)piperazine
[6]comparative experiment These experiments show that operating at amine functional compound to diethanolamine mole ratios of 0.2:1 or more, and also carbon oxide delivering agent to —NH—CH2-CH2-NH— unit mole ratios of 0.1:1 or more results in superior yields of higher ethyleneamines and hydroxyethylethyleneamines, including their urea derivatives.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the disclosure as set forth in the appended claims and their legal equivalents.

The invention claimed is:

1. A process for preparing hydroxyethylethyleneamines, ethyleneamines, or mixtures thereof, and/or ethylene urea derivatives thereof comprising the step of reacting diethanolamine with an amine-functional compound comprising at least two —NH— units of which at least one is selected from the group of primary amine groups and cyclic secondary amine groups, the amine-functional compound comprising at least one —NH—CH2-CH2-NH— unit wherein one or more —NH—CH2-CH2-NH— units in the amine-functional compound is present in the form of cyclic ethylene urea moieties, piperazine moieties, or linear ethylene urea moieties, in the presence of a carbon oxide delivering agent, wherein the molar ratio of amine-functional compound to diethanolamine is at least about 0.2:1, the molar ratio of carbon oxide delivering agent to —NH—CH2-CH2-NH— units in the amine-functional compound is at least about 0.1:1, the amino-functional compound and the carbon oxide delivering agent are not the same compound, and the amine-functional compound comprises ethylenediamine (EDA), ethylene urea (EU), or a mixture thereof, and the reaction product comprises tetraethylenepentamine (TEPA) of the formula H2N—(CH2-CH2-NH-)p-H, wherein p is 4, wherein one or more —NH—CH2-CH2-NH— units is present as cyclic ethylene urea units and/or piperazine units, and wherein one or more ethyleneamines or ethylene urea derivatives thereof are connected to each other via a linear ethylene urea structure.

2. The process according to claim 1, wherein the molar ratio of amine-functional compound to diethanolamine is at least about 0.5:1.

3. The process according to claim 1, wherein the molar ratio of the carbon oxide delivering agent to —NH—CH2-CH2-NH— units in the amine-functional compound is from about 0.2:1 to about 3:1.

4. The process according to claim 1, wherein diethanolamine is provided at least in part in a form of a CO adduct.

5. The process according to claim 1, wherein the carbon oxide delivering agent includes carbon dioxide, and organic compounds which are condensation products of carbon dioxide and an organic compound that includes an amino group or a hydroxyl group.

6. The process according to claim 5, wherein the carbon oxide delivering agent is selected from the group of carbon dioxide, carbon dioxide adducts of diethanolamine, and urea-derivatives of ethyleneamine compounds.

7. The process according to claim 1, wherein at least two —NH— units in the amine-functional compound are selected from the group of primary amine groups and cyclic secondary amine groups.

8. The process according to claim 1, wherein at least about 50% of CO is added in the form of CO adducts of diethanolamine and/or the amine-functional compound.

9. The process according to claim 1, wherein the reaction product comprises ethyleneamines of a formula H2N—(CH2-CH2-NH-)p-H wherein p is at least 4 or derivatives thereof.

10. The process according to claim 1, wherein the amine-functional compound comprises ethylenediamine (EDA).

11. A process for preparing hydroxyethylethyleneamines, ethyleneamines, or mixtures thereof, and/or ethylene urea derivatives thereof comprising the step of reacting diethanolamine with an amine-functional compound comprising at least two —NH— units of which at least one is selected from the group of primary amine groups and cyclic secondary amine groups, the amine-functional compound comprising at least one —NH—CH2-CH2-NH— unit wherein one or more —NH—CH2-CH2-NH— units in the amine-functional compound is present in the form of cyclic ethylene urea moieties, piperazine moieties, or linear ethylene urea moieties, in the presence of a carbon oxide delivering agent, wherein the molar ratio of amine-functional compound to diethanolamine is at least about 0.2:1, the molar ratio of carbon oxide delivering agent to —NH—CH2-CH2-NH— units in the amine-functional compound is at least about 0.1:1, the amino-functional compound and the carbon oxide delivering agent are not the same compound, the amine-functional compound comprises ethylenediamine (EDA), ethylene urea (EU), or a mixture thereof, and the reaction product comprises tetraethylenepentamine (TEPA) of the formula H2N—(CH2-CH2-NH-)p-H wherein p is 4, wherein one or more —NH—CH2-CH2-NH— units is present as cyclic ethylene urea units and/or piperazine units, and wherein one or more ethyleneamines or ethylene urea derivatives thereof are connected to each other via a linear ethylene urea structure, or the amine-functional compound comprises diethylenetriamine (DETA), the urea adduct thereof (UDETA), or a mixture thereof, and the reaction product comprises hexaethyleneheptamine (HEHA) of the formula H2N—(CH2-CH2-NH-)p-H wherein p is 6, wherein one or more —NH—CH2-CH2-NH— units is present as a cyclic ethylene urea units and/or or piperazine units, and wherein one or more ethyleneamines or ethylene urea derivatives thereof are connected to each other via a linear ethylene urea structure.

12. A process for preparing hydroxyethylethyleneamines, ethyleneamines, or mixtures thereof, and/or ethylene urea derivatives thereof comprising the step of reacting diethanolamine with an amine-functional compound comprising at least two —NH— units of which at least one is selected from the group of primary amine groups and cyclic secondary amine groups, the amine-functional compound comprising at least one —NH—CH2-CH2-NH— unit wherein one or more —NH—CH2-CH2-NH— units in the amine-functional compound is present in the form of cyclic ethylene urea moieties, piperazine moieties, or linear ethylene urea moieties, in the presence of a carbon oxide delivering agent, wherein the molar ratio of amine-functional compound to diethanolamine is at least about 0.2:1, the molar ratio of carbon oxide delivering agent to —NH—CH2-CH2-NH— units in the amine-functional compound is at least about 0.1:1, the amino-functional compound and the carbon oxide delivering agent are not the same compound, the amine-functional compound comprises ethylenediamine (EDA), ethylene urea (EU), or a mixture thereof, and the reaction product comprises tetraethylenepentamine (TEPA) of the formula H2N—(CH2-CH2-NH-)p-H wherein p is 4, wherein one or more —NH—CH2-CH2-NH— units is present as cyclic ethylene urea units and/or piperazine units, and wherein one or more ethyleneamines or ethylene urea derivatives thereof are connected to each other via a linear ethylene urea structure, or the amine-functional compound comprises piperazine (PIP) and the reaction product comprises hydroxyethyleneaminoethylpiperazine (HEAEPIP) and/or piperazinoethylaminoethylpiperazine (PEAEP).

13. The process according to claim 1, further comprising the step of subjecting the reaction product to a CO removal reaction to convert urea adducts present therein into ethylene amines and/or ethanolamines.

14. The process according to claim 1, wherein the molar ratio of amine-functional compound to diethanolamine is at least about 1:1.

15. The process according to claim 1, wherein the molar ratio of amine-functional compound to diethanolamine is at least about 1.5:1.

16. The process according to claim 1, wherein the molar ratio of amine-functional compound to diethanolamine is at least about 2:1.

17. The process according to claim 1, wherein at least about 75% of CO is added in the form of CO adducts of diethanolamine and/or the amine-functional compound.

18. The process according to claim 1, wherein at least about 90% of CO is added in the form of CO adducts of diethanolamine and/or the amine-functional compound.

19. The process according to claim 1, wherein the amine-functional compound comprises ethylene urea (EU).

* * * * *